United States Patent
Amanullah et al.

(10) Patent No.: US 11,215,018 B2
(45) Date of Patent: Jan. 4, 2022

(54) DEVICES AND METHODS FOR PLACEMENT OF LOSS CONTROL SLURRY

(71) Applicant: Saudi Arabian Oil Company, Dhahran (SA)

(72) Inventors: Md Amanullah, Dhahran (SA); Turki Al-Subaie, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/094,476

(22) Filed: Nov. 10, 2020

(65) Prior Publication Data

US 2021/0102431 A1    Apr. 8, 2021

Related U.S. Application Data

(62) Division of application No. 16/594,593, filed on Oct. 7, 2019, now Pat. No. 10,907,425.

(51) Int. Cl.
*E21B 21/00*    (2006.01)
*E21B 33/13*    (2006.01)

(52) U.S. Cl.
CPC ............ *E21B 21/003* (2013.01); *E21B 33/13* (2013.01)

(58) Field of Classification Search
CPC .................................................. E21B 21/003
See application file for complete search history.

(56) References Cited

U.S. PATENT DOCUMENTS

| 6,449 A | 5/1849 | Scudder |
| 1,443,315 A | 1/1923 | Ehrhart |
| 2,155,279 A | 4/1939 | McMahan |
| 2,733,595 A | 2/1956 | Twining |
| 3,345,931 A | 10/1967 | Walsh |
| 7,992,760 B2 | 8/2011 | Wilks |
| 9,038,927 B2* | 5/2015 | Denzler .................. E03C 1/086 239/428.5 |
| 9,243,950 B2 | 1/2016 | Raniere |
| 2002/0162860 A1 | 11/2002 | Gehn et al. |
| 2007/0199368 A1* | 8/2007 | Freeman ............ G01N 33/2823 73/37 |

(Continued)

FOREIGN PATENT DOCUMENTS

| CN | 204008597 U | 12/2014 |
| CN | 105155321 A | 12/2015 |

(Continued)

OTHER PUBLICATIONS

International Search Report & Written Opinion for International Application No. PCT/US2020/054606, dated Feb. 17, 2021; pp. 1-7.

*Primary Examiner* — William D Hutton, Jr.
*Assistant Examiner* — Avi T Skaist
(74) *Attorney, Agent, or Firm* — Bracewell LLP; Constance G. Rhebergen; Brian H. Tompkins

(57) ABSTRACT

An LCM placement device for placement of an LCM onto a test bed in a test cell is provided. The LCM placement device minimizes or prevents damage and degradation of the test bed during placement of the LCM. The device includes a funnel-shaped feeder, a cylindrical shaft, an inverted funnel-shaped dispenser, and an energy-absorbing disc coupled to the inverted funnel-shaped dispenser by legs. Processes for placement of an LCM onto a test bed in a test cell are also provided.

4 Claims, 5 Drawing Sheets

(56) References Cited

U.S. PATENT DOCUMENTS

2013/0239600 A1\* 9/2013 Verma .................. F04F 5/16
                                                      62/115
2014/0102188 A1    4/2014 Murphy et al.

FOREIGN PATENT DOCUMENTS

| CN | 105735968 A | 7/2016 |
| CN | 107882758 A | 4/2018 |
| CN | 207565318 U | 7/2018 |
| CN | 108518578 A | 9/2018 |
| CN | 208327827 U | 1/2019 |

\* cited by examiner

DEVICES AND METHODS FOR PLACEMENT OF LOSS CONTROL SLURRY

CROSS-REFERENCE TO RELATED APPLICATIONS

This application is a divisional of and claims priority from U.S. Non-provisional application Ser. No. 16/594,593 filed Oct. 7, 2019, and titled "DEVICES AND METHODS FOR PLACEMENT OF LOSS CONTROL SLURRY," a copy of which is incorporated by reference in its entirety for purposes of United States patent practice.

BACKGROUND

Field of the Disclosure

The present disclosure generally relates to the testing and evaluation of lost circulation materials (LCMs) used to control lost circulation in a wellbore during drilling with a drilling fluid. More specifically, embodiments of the disclosure relate to the placement of LCM slurries on a test bed.

Description of the Related Art

Lost circulation is one of the frequent challenges encountered during drilling operations. Lost circulation can be encountered during any stage of operations and occurs when drilling fluid (or drilling mud) pumped into a well returns partially or does not return to the surface. While some fluid loss is expected, excessive fluid loss is not desirable from a safety, an economical, or an environmental point of view. Lost circulation is associated with problems with well control, borehole instability, pipe sticking, unsuccessful production tests, poor hydrocarbon production after well completion, and formation damage due to plugging of pores and pore throats by mud particles. Lost circulation problems may also contribute to non-productive time (NPT) for a drilling operation. In extreme cases, lost circulation problems may force abandonment of a well.

SUMMARY

Lost circulation materials (LCMs) are used to mitigate lost circulation by blocking the path of the drilling fluid (such as drilling mud) into the formation. The type of LCM used in a lost circulation situation depends on the extent of lost circulation and the type of formation. Different types of LCMs such as granular, fibrous, and flaky materials are frequently used either alone or in combination to control loss of circulation.

Various types of test beds may be used to simulate different types of loss zones and evaluate different LCMs for suitability and selection for a particular type of loss zone. For example, a 20/40 sand bed may be used to simulate a highly permeable loss zone that is prone to cause partial loss of circulation. In another example, a bed of carbonate chips having sizes in the range of 4 millimeters (mm) to 8 mm may be used to simulate an extremely permeable loss zones that causes moderate to severe loss of circulation. In another example, a bed of pebbles having sizes in the range of 20 mm to 30 mm may be used to simulate a rubble or "super-K" loss zone that causes severe loss of circulation. As used herein, the term "super-K" refers to zones that produce greater than 500 barrels per day per foot of thickness (BLPD/ft). The quality of the test bed is an important factor for reliable evaluation of LCM performance. Ideally, there should be no or negligible degradation of the test bed during the placement of an LCM on top of the test bed. The quality of test bed is directly related to the quality of the LCM testing, the quality of the experimental data, and the reduction of the margin for errors of the experimental data.

An existing technique for the placement of an LCM (for example, an LCM pill or slurry) on a test bed is to introduce the LCM close to the test bed cell wall using a flexible tube. However, this technique may cause significant damage or degradation to the top of the test bed depending on the skills of the technician and is unable to ensure a quality test bed for superior data generation due to the damage and degradation. FIG. 1 is a photograph 100 that depicts the damage caused at the top of a test bed while using this flexible tube technique with water as a representative of a LCM slurry. The damaged zone is shown in area 102 and illustrates the damage caused by this technique.

Another proposed technique for placement of an LCM on top of a test bed is pouring an LCM slurry at the wall of a test cell by tilting the test cell at an angle of 10 degrees to 15 degrees so that a significant amount of kinetic energy is lost during the movement of the LCM slurry from the top of the test cell to the top of the test bed. However, this technique is difficult to implement, generates uncontrolled tilting of the test cell, and causes movement of the test bed material due to the tilting of the test cell. This technique also causes damage at the periphery of the test bed. FIG. 2 is a photograph 200 that depicts the damage caused at the periphery of a test bed while using this technique with an LCM slurry. The damaged zone is shown in area 202 and illustrates the damage caused by the tilting of the test cell and placement of the LCM slurry.

Embodiments of the disclosure are directed to devices and processes for placement of an LCM slurry on the top of a test bed to minimize or prevent damage and degradation of the test bed. As described in the disclosure, placement of an LCM slurry using the devices and processes maintain the quality of the test bed and improve the quality of the LCM testing and experimental data as compared to prior art techniques.

In one embodiment, an apparatus for placement of a lost circulation material (LCM) on a test bed in a test cell, the apparatus is provided. The apparatus includes a funnel-shaped portion that includes a mouth having a first diameter and an outlet having a second diameter, the first diameter greater than the second diameter, and a cylindrical shaft having a first end and a second end, the funnel-shaped portion positioned at a first end of the cylindrical shaft. The apparatus also includes an inverted funnel-shaped portion positioned at a second end of the cylindrical shaft, the inverted funnel-shaped portion including an inlet having a third diameter and a mouth having a fourth diameter, and a disc coupled to the inverted-funnel shaped portion via a plurality of legs, such that a surface of the disc is facing the mouth of the inverted funnel-shaped portion to define a distance between the surface of the disc and the mouth of the inverted funnel-shaped portion. The apparatus is configured to convert axial flow through the cylindrical shaft to radial flow across the surface of the disc.

In some embodiments, the disc is formed from stainless steel. In some embodiments, the plurality of legs includes three legs around the circumference of the cylindrical shaft such that each leg is located 120 degrees from an adjacent leg. In some embodiments, the test bed is a sand bed. In some embodiments, the disc has a disc diameter, such that the disc diameter is selected to provide for insertion of the disc into the test cell containing the test bed. In some embodiments, the funnel-shaped portion has a length of 70 millimeters (mm) and the first diameter of the mouth is 68 mm. In some embodiments, the cylindrical shaft has a length of 100 millimeters and an inner diameter of 10 mm. In some embodiments, the inverted funnel-shaped portion has a length of 10 millimeters (mm) and the fourth diameter of the mouth is 15 mm. In some embodiments, the disc has a length of 5 millimeters and a diameter of 68 mm.

In another embodiment, a method for placing a lost circulation material (LCM) on a test bed in a test cell is provided. The method includes preparing a mixture having the LCM and inserting an LCM placement apparatus into the test cell. The LCM placement apparatus includes a funnel-shaped portion that includes a mouth having a first diameter and an outlet having a second diameter, the first diameter greater than the second diameter, and a cylindrical shaft having a first end and a second end, the funnel-shaped portion positioned at a first end of the cylindrical shaft. The LCM placement apparatus also includes an inverted funnel-shaped portion positioned at a second end of the cylindrical shaft, the inverted funnel-shaped portion including an inlet having a third diameter and a mouth having a fourth diameter, and a disc coupled to the inverted-funnel shaped portion via a plurality of legs, such that a surface of the disc is facing the mouth of the inverted funnel-shaped portion to define a distance between the surface of the disc and the mouth of the inverted funnel-shaped portion. The method further includes pouring the mixture onto an inner wall of the funnel-shaped portion of the LCM placement apparatus, such that the slurry flows axially through the cylindrical shaft and flows radially across a surface of the disc after exiting the inverted funnel-shaped portion.

In some embodiments, the mixture is a slurry. In some embodiments, the disc is formed from stainless steel. In some embodiments, the plurality of legs includes three legs around the circumference of the cylindrical shaft such that each leg is located 120 degrees from an adjacent leg. In some embodiments, the test bed is a sand bed. In some embodiments, the disc has a disc diameter, such that the disc diameter is selected to provide for insertion of the disc into the test cell containing the test bed. In some embodiments, inserting an LCM placement apparatus into the test cell includes an LCM placement apparatus into the test cell to define a space between the test bed and a surface of the disc.

In another embodiment, a method of manufacturing an apparatus for placement of a lost circulation material (LCM) on a test bed in a test cell is provided. The method includes connecting a funnel-shaped portion to a first end of a cylindrical shaft, the funnel-shaped portion including a mouth having a first diameter and an outlet having a second diameter, the first diameter greater than the second diameter and connecting an inverted funnel-shaped portion to a second end of the cylindrical shaft, the inverted funnel-shaped dispenser including an inlet having a third diameter and a mouth having a fourth diameter. The method also includes coupling a disc to the inverted-funnel shaped portion via a plurality of legs, such that a surface of the disc faces the mouth of the inverted funnel-shaped dispenser to define a distance between the surface of the disc and the mouth of the inverted funnel-shaped dispenser. The apparatus is configured to convert axial flow through the cylindrical shaft to radial flow across the surface of the disc.

In some embodiments, coupling a disc to the inverted-funnel shaped portion via a plurality of legs includes welding the legs to the inverted-funnel shaped portion. In some embodiments, the disc is formed from stainless steel. In some embodiments, the plurality of legs includes three legs around the circumference of the cylindrical shaft such that each leg is located 120 degrees from an adjacent leg.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure are directed to an LCM placement device and process for placement of an LCM (for example, in an LCM slurry) on the top of a test bed in a test cell. The device and process minimize or prevent damage and degradation of the test bed during placement of the LCM. The device includes a funnel-shaped feeder, a cylindrical shaft, an inverted funnel-shaped dispenser, and an energy-absorbing disc coupled to the inverted funnel-shaped dispenser by legs.

As described in the disclosure, the LCM placement device for placement of an LCM may reduce the kinetic and potential energies of an LCM slurry before it reaches the top of the test bed to minimize or prevent damage and degradation to the test bed. As described infra, the LCM placement device may convert axial flow to radial flow via an energy-absorbing disc to further dissipate the kinetic and potential energies. The energy-absorbing disc also acts to divert the flow of the LCM slurry.

Although the LCM placement device and process may be described with reference to an LCM slurry, it should be appreciated that other mixtures may be used in with the LCM placement device and process described in the disclosure. For example, the LCM placement device and process may be used with an LCM fluid pill, an LCM with or without a carrier fluid, LCM suspensions, and LCM fluids.

As will be appreciated, translational kinetic energy (that is, kinetic energy from translational motion) depends on the mass and velocity of the moving object. The kinetic energy is directly proportional to the square of the velocity. The device and process described in the disclosure may significantly reduce the kinetic energy of an LCM slurry moving through the device to avoid any damage and degradation of a test bed.

As will also be appreciated, the potential energy of the object is the energy of an object's position relative to the position of another objects. For an object falling from a higher position, there is a direct relationship between the potential energy and the dropping height; the potential energy increases with an increase in dropping height or decreases with a decrease in dropping height. The device and process described in the disclosure reduces the potential energy of the LCM slurry by reducing the dropping height between the LCM and the top of a test bed (for example, some embodiments may reduce the dropping height from about 100 mm to about 5 mm).

Figure 1:
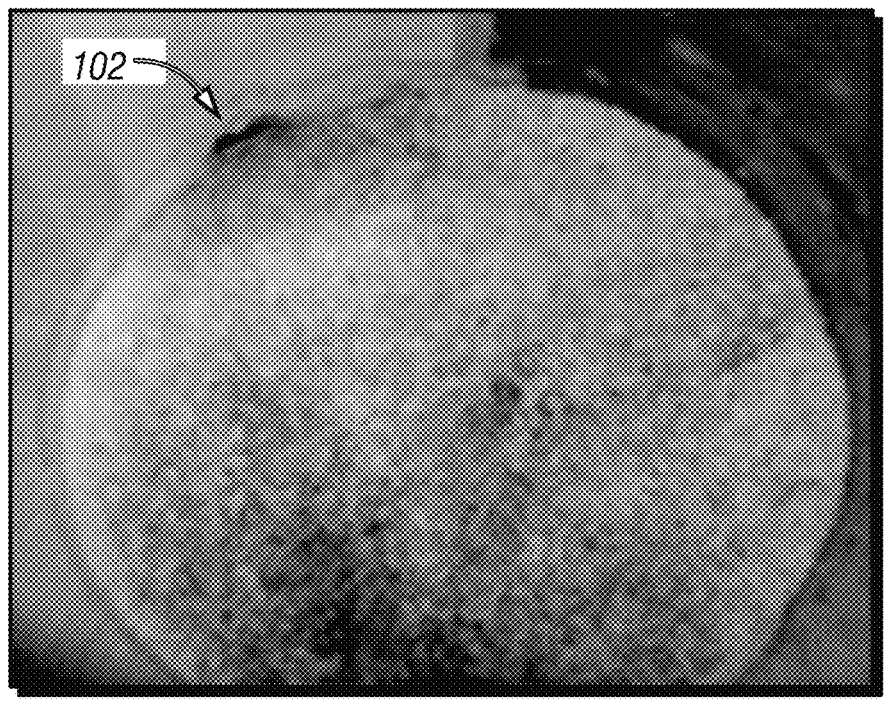
FIG. 1 is a photograph that depicts the damage caused at the top of a test bed while using a prior art technique with water as a representative of a LCM slurry.
Figure 2:
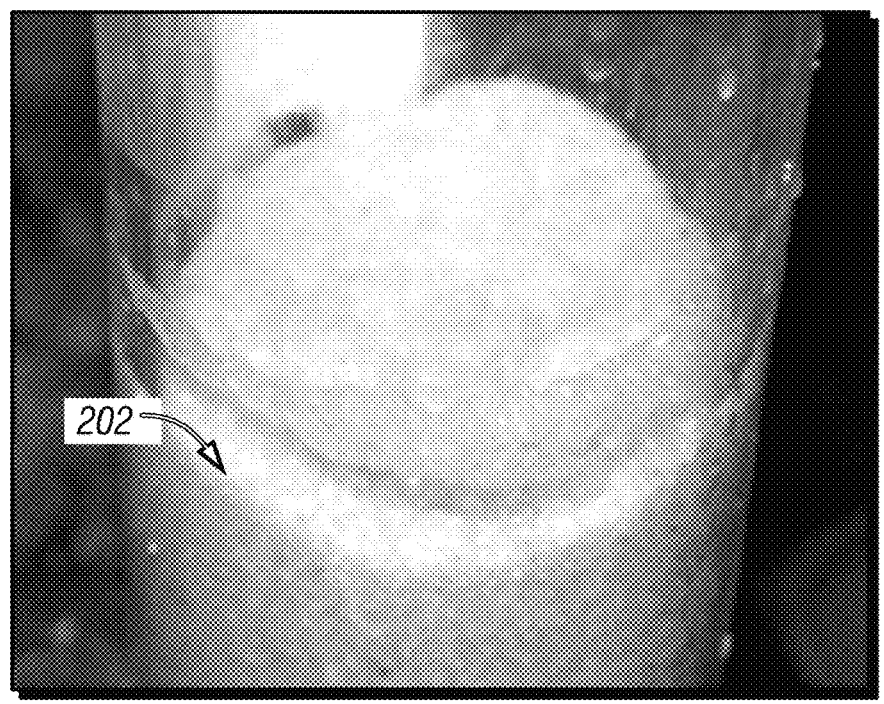
FIG. 2 is a photograph that depicts the damage caused at the top of a test bed while using a prior art technique.
Figure 3:
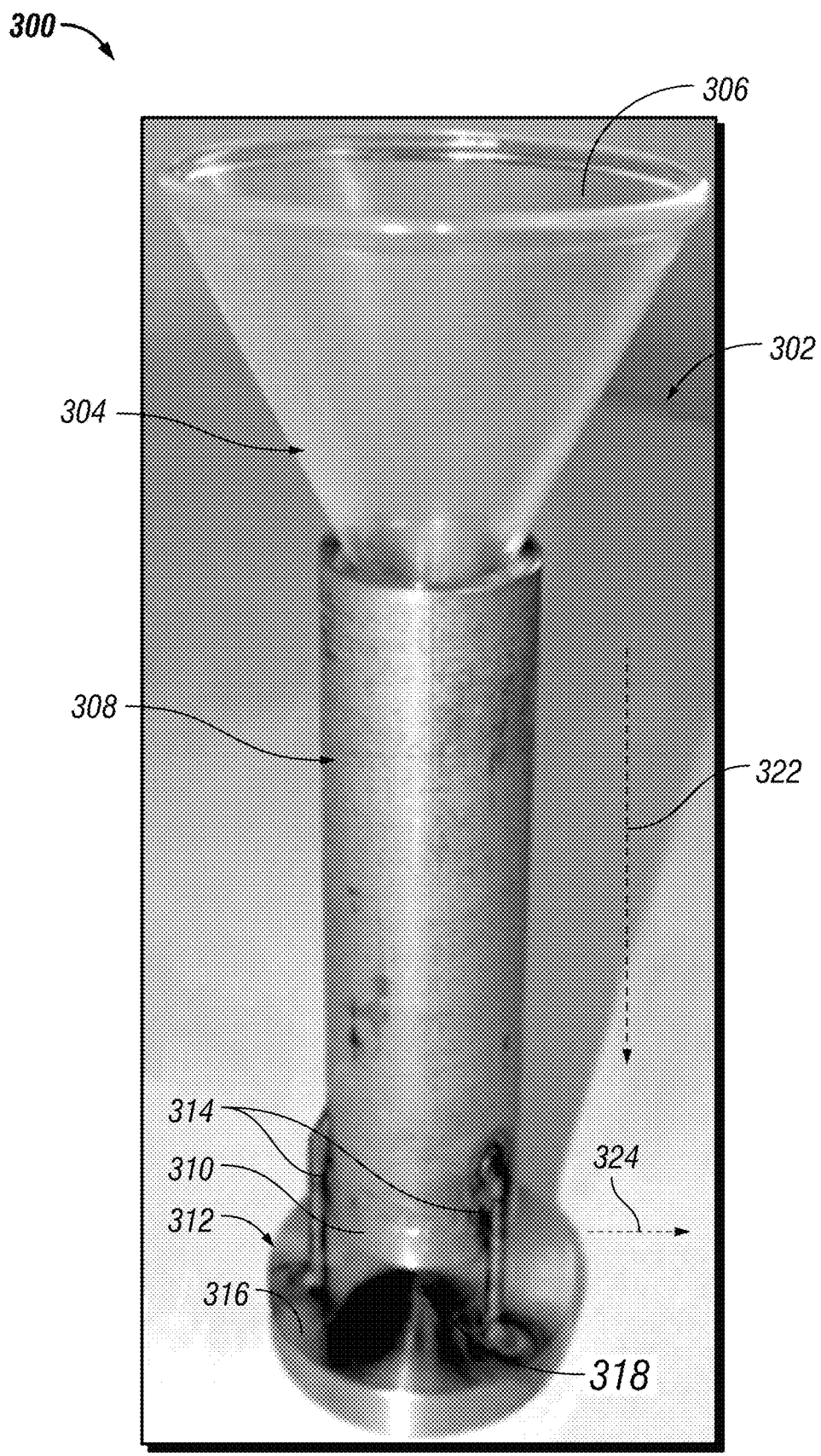
FIG. 3 is a photograph of an LCM placement device in accordance with an embodiment of the disclosure.
Figure 4:
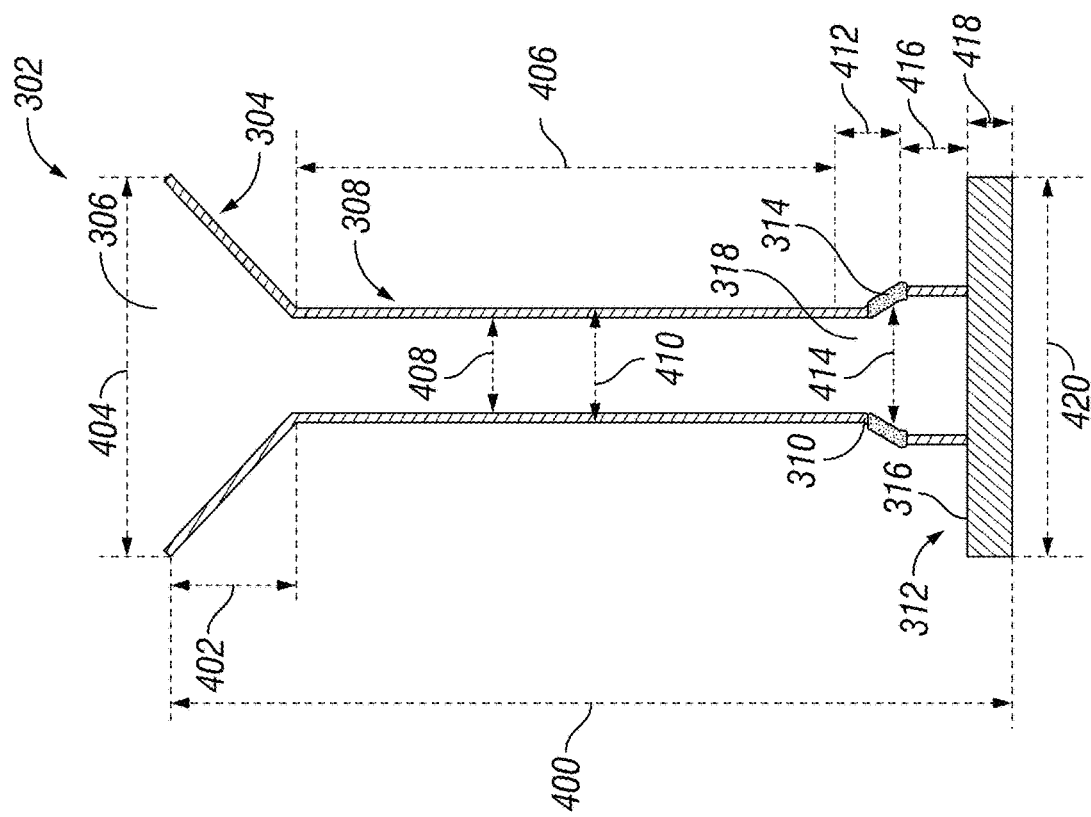
FIG. 4 is a schematic side view of an LCM placement device in accordance with an embodiment of the disclosure.

FIG. 3 is a photograph 300 of an LCM placement device 302 and FIG. 4 is a schematic side view of the LCM placement 302 in accordance with an embodiment of the disclosure. As shown in FIGS. 3 and 4, the device 302 includes a funnel-shaped feeder 304 having a mouth 306, a cylindrical shaft 308, an inverted funnel-shaped dispenser 310, and an energy-absorbing disc 312. The energy-absorbing disc 312 may be coupled to the inverted funnel-shaped dispenser 310 via legs 314. The energy-absorbing disc 312 is oriented such that a surface 316 (that is, a "face") of the energy-absorbing disc 312 faces the mouth 318 of the inverted funnel-shaped dispenser 310 and defines a distance between the surface 316 of the energy-absorbing disc 312 and the mouth 318 of the inverted funnel-shaped dispenser 310.

The space 320 between the legs 314 may define a radial flow path across the surface 316 of the energy-absorbing disc 312 for an LCM slurry to exit the LCM placement device 302 onto a test bed with no or negligible disturbance to the test bed. In some embodiments, the LCM placement device 302 may include three legs 314 spaced at 120 degrees around the circumference of the cylindrical shaft 308 and the perimeter of the surface 316 of the energy-absorbing disc 312.

In some embodiments, the cylindrical shaft 308, the inverted funnel shaped dispenser 310, the energy-absorbing disc 312, and legs 314 may be formed from a corrosive resistant material, such as certain metals. For example, in some embodiments the cylindrical shaft 308, the inverted funnel shaped dispenser 310, the energy-absorbing disc 312, and legs 314 may be formed from stainless steel or aluminum. In such embodiments, as shown in FIG. 3, one end of the legs 314 may be welded to an outer wall of the cylindrical shaft 308 and the other end of the legs 314 may be welded to the surface 316 of the energy-absorbing disc 312. In some embodiments, the funnel-shaped feeder 304 may be formed from metal or plastic.

FIG. 3 also depicts the general flow of an LCM slurry when using the LCM placement device 302 to place an LCM slurry on the top of a test bed. As shown by arrow 322 in FIG. 3, an LCM slurry may first flow in a generally axial direction when poured into the funnel shaped feeder 304. The energy-absorbing disc 312 may absorb energy from the LCM slurry after the LCM slurry exits the mouth 318 of the inverted funnel-shaped dispenser 310 and contacts the surface 316 of the energy-absorbing disc 312. After the LCM slurry contacts the surface 316 of the energy-absorbing disc 312, the LCM slurry may flow in a generally radial direction across the surface 316 of the energy-absorbing disc 312 as generally indicated by arrow 324.

FIG. 4 depicts various dimensions of the LCM placement device 302. The LCM placement device 302 may have a length 400, as defined from the top of the funnel-shaped feeder 304 to the bottom of the energy-absorbing disc 312. In some embodiments, the height 400 may be about 200 mm.

The funnel-shaped feeder 304 may have a length 402 and mouth diameter 404. In some embodiments, the length 402 may be about 70 mm and the mouth diameter 404 may be about 68 mm. The cylindrical shaft 308 may have a length 406, an inner diameter 408, and an outer diameter 410. In some embodiments, the length 406 may be about 100 mm, the inner diameter 408 may be about 10 mm, and the outer diameter 410 may be about 15 mm.

As shown in FIG. 4, the inverted funnel-shaped dispenser 310 may have a length 412 and a mouth diameter 414. In some embodiments, the length 412 may be about 10 mm and the mouth diameter 414 may be about 15 mm. The legs 314 may have a length 416. In some embodiments, the length 416 of the legs 314 may be about 15 mm. The energy-absorbing disc 312 may have a length 418 and a diameter 420. In some embodiments, the length 418 may be about 5 mm and the diameter 420 may be about 68 mm.

Figure 5:
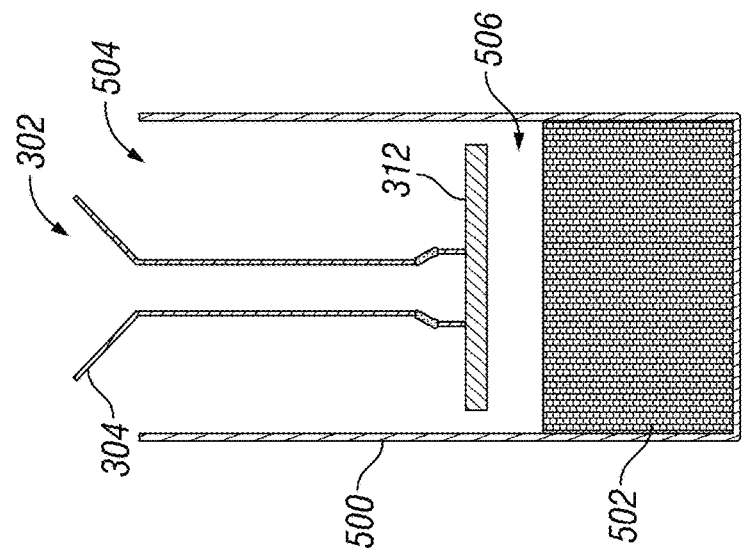
FIG. 5 is a schematic side view of an LCM placement device inserted into a test cell in accordance with an embodiment of the disclosure.

FIG. 5 depicts the LCM placement apparatus 302 inserted into a test cell 500 in accordance with an embodiment of the disclosure. As shown in FIG. 5, the test cell 500 contains a test bed 502 for testing an LCM. The LCM placement apparatus 302 may be inserted into the test cell 500 via an opening 504 at the top of the test cell 500. For example, the test cell 500 may be closed with a lid or other component that is removed for placement of an LCM slurry via the LCM placement apparatus 302.

The LCM placement apparatus 302 may be inserted into the test cell 500 such that the funnel-shaped feeder 304 extends above the opening 504 of the test cell 500 and the energy-absorbing disc 312 does not contact the test bed 502. For example, in some embodiments a space 506 may be provided between the energy-absorbing disc 312 and the test bed 502 for the LCM slurry to exit the LCM placement device.

Figure 6:
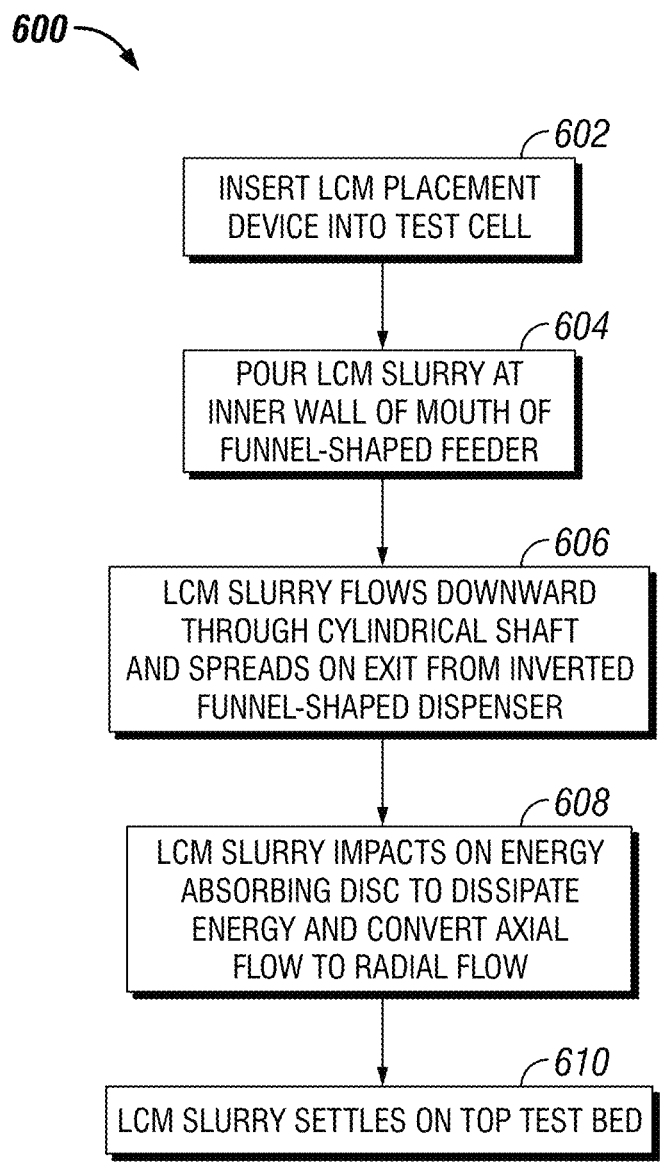
FIG. 6 is a block diagram of a process for using an LCM to place an LCM slurry on a test bed in a test cell in accordance with an embodiment of the disclosure.

FIG. 6 depicts a process 600 for using the LCM placement device to place an LCM slurry on a test bed in a test cell in accordance with an embodiment of the disclosure. Initially, the LCM placement device may be inserted into a test cell having a test bed (block 602). The LCM placement device may be inserted such that the funnel-shaped feeder extends above the top of the test cell and the energy-absorbing disc does not contact the test bed and provides sufficient space for an LCM slurry to exit the LCM placement device onto the test bed.

Next, an LCM slurry for testing is poured at an inner wall of the mouth of the funnel-shaped feeder 302 (block 604). In some embodiments, an LCM slurry may be prepared by mixing an LCM with a drilling fluid, such as bentonite mud having water, bentonite, caustic soda, and soda ash. After pouring into the LCM placement device, the LCM slurry flows downward through the cylindrical shaft 308 and spreads upon exit from the inverted funnel-shaped dispenser 310 (block 606). The LCM slurry then impacts the energy-absorbing disc 312 which dissipates energy and convers the axial flow from the cylindrical shaft 308 and inverted funnel-shaped dispenser 310 to radial flow (block 608). The LCM slurry then settles onto the top of the test bed (block 610). Thus, the device and process for placement of an LCM slurry provides a simultaneous reduction of kinetic and potential energies during placement of the LCM slurry on a test bed and changes the flow direction from axial to radial to preserve the quality of the test bed and minimize or prevent any damage and degradation.

After placement of the LCM slurry, the LCM may be tested for sealing, plugging, and blocking capabilities of the LCM. For example, the test cell may be pressurized and heated to a specific pressure and temperature, and properties such as fluid loss, spurt loss, total leak off may be measured via fluid collection from an outlet port at the bottom of the test cell. Additionally, the thickness of a cake formed by the LCM slurry after pressurization may be measured.

The LCM placement device and process described in the disclosure may be used with different types of test beds, including sand beds, pebble beds, and carbonate chips beds. The LCM placement device and process may be used with various test apparatus having a generally cylindrical-shaped test cell. An example test apparatus may have a test cell configured to be pressurized via a gas pressure line connected through a top lid of the test cell and heated via placement in a heating jacket. In some embodiments, a test cell may have a slotted disc. In some embodiments, a test cell may have an outlet at the bottom of the test cell for connection via tubing to a fluid collection device. In some embodiments, an example test apparatus may be a Permeability Plugging Tester (also referred to as "PPT" or "Pore Plugging Test" apparatus) manufactured by OFI Testing Equipment, Inc., of Houston, Tex., USA.

Figure 7:
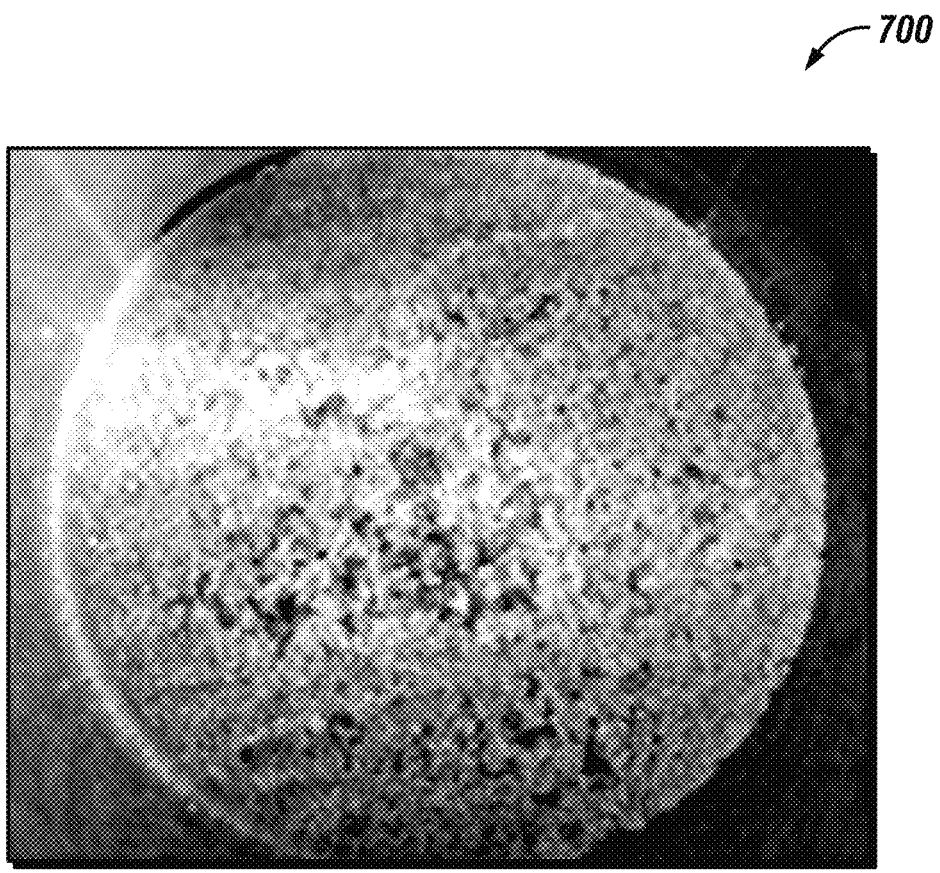
FIG. 7 is a photograph of a sand bed after placement of an LCM slurry using an LCM placement device and process described in the disclosure.

An LCM slurry placement test was conducted using the LCM placement device and process with a sand bed as the test bed. FIG. 7 is a photograph 700 of the sand bed after placement of the LCM slurry using the LCM placement device and process described in the disclosure. As shown in FIG. 7, the top of the test bed shows zero or negligible damage and degradation, thus demonstrating the effectiveness of the LCM placement device and process in maintaining the quality of a test bed.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method of manufacturing an apparatus for placement of a lost circulation material (LCM) on a test bed in a test cell, the method comprising:
   connecting a funnel-shaped portion to a first end of a cylindrical shaft, the funnel-shaped portion comprising a mouth having a first diameter and an outlet having a second diameter, the first diameter greater than the second diameter;
   connecting an inverted funnel-shaped portion to a second end of the cylindrical shaft, the inverted funnel-shaped dispenser comprising an inlet having a third diameter and a mouth having a fourth diameter; and
   coupling a solid disc to the inverted-funnel shaped portion via a plurality of legs, such that a surface of the solid disc faces the mouth of the inverted funnel-shaped dispenser to define a distance between the surface of the solid disc and the mouth of the inverted funnel-shaped dispenser, wherein apparatus is configured to convert axial flow through the cylindrical shaft to radial flow across the surface of the solid disc.

2. The method of claim 1, wherein the step of coupling a solid disc to the inverted-funnel shaped portion via a plurality of legs comprises welding the legs to the inverted-funnel shaped portion.

3. The method of claim 1, wherein the solid disc is formed from stainless steel.

4. The method of claim 1, wherein the plurality of legs comprises three legs around the circumference of the cylindrical shaft such that each leg is located 120 degrees from an adjacent leg.

* * * * *